United States Patent [19]

Sikkenga et al.

[11] Patent Number: 5,030,781

[45] Date of Patent: Jul. 9, 1991

[54] PREPARATION OF A DIMETHYLTETRALIN

[75] Inventors: David L. Sikkenga; Ian C. Zaenger, both of Wheaton, Ill.; Gregory S. Williams, Tampa, Fla.

[73] Assignee: Amoco Corporation, Chicago, Ill.

[21] Appl. No.: 539,007

[22] Filed: Jun. 15, 1990

[51] Int. Cl.$^5$ ................................................ C07C 5/00
[52] U.S. Cl. ................................. 585/320; 585/410; 585/411
[58] Field of Search .............. 585/400, 411, 410, 320, 585/430

[56] References Cited

U.S. PATENT DOCUMENTS 3,997,616  12/1976  Tokashiki et al. ................. 585/411

FOREIGN PATENT DOCUMENTS 50-22551  10/1970  Japan ................................. 585/411
50-58050   9/1973  Japan ................................. 585/411

Primary Examiner—Curtis R. Davis
Attorney, Agent, or Firm—James R. Henes; William H. Magidson; Ralph C. Medhurst

[57] ABSTRACT

A method for preparing one or more specific dimethyltetralins by cyclization of either 5-(o-, m, or p-tolyl)-pent-1- or -2-ene or 5-phenyl-hex-1- or -2-ene, with additional cyclization treatment, and optionally cracking, of a heavy fraction of the cyclization product, is disclosed.

16 Claims, No Drawings

PREPARATION OF A DIMETHYLTETRALIN

BACKGROUND OF THE INVENTION

1. Related Application

This application is related to U.S. patent application Ser. No. 539,087 of D. L. Sikkenga, G. S. Williams and I. C. Zaenger, filed concurrently herewith.

2. Field of the Invention

This invention relates generally to a method for preparing a dimethyltetralin and more particularly concerns a method for preparing with improved selectivity a specific dimethyltetralin or a mixture of specific dimethyltetralins by the cyclization of either 5-(o-, m-, or p-tolyl)-pent-1- or -2-ene or 5-phenyl-hex-1- or -2-ene.

3. Description of the Prior Art

Naphthalene dicarboxylic acids are monomers that are known to be useful for the preparation of a variety of polymers. For example, poly(ethylene 2,6-naphthalate) prepared from 2,6-naphthalene dicarboxylic acid and ethylene glycol has better heat resistance and mechanical properties than polyethylene terephthalate and is useful in the manufacture of films and fibers.

Dimethylnaphthalenes are desirable feedstocks for oxidation to the corresponding naphthalene dicarboxylic acids. A known conventional process for producing a naphthalene dicarboxylic acid comprises the oxidation of a dimethylnaphthalene with oxygen in the liquid phase in an acetic acid solvent at an elevated temperature and pressure and in the presence of a catalyst comprising cobalt, manganese and bromine components.

Typically, dimethylnaphthalenes are found in refinery or coal-derived streams as mixtures of all of the ten possible dimethylnaphthalene isomers. However, separation of these isomers is very difficult and expensive. Consequently, methods for producing specific dimethylnaphthalenes or mixtures of two or three specific dimethylnaphthalenes in high purity and quality are highly desirable. One such method is a multistep synthesis involving: (1) the formation of an alkenylbenzene by the reaction of o-, m- or p-xylene or ethylbenzene with butadiene; (2) the cyclization of the resulting alkenylbenzene to form one or more dimethyltetralins belonging to one or two of three groups of isomeric dimethyltetralins—that is, either the group containing the 1,5-, 1,6-, 2,5- and 2,6-dimethyltetralins, the group containing the 1,7-, 1,8- 2,7- and 2,8-dimethyltetralins, or the group containing the 1,3-, 1,4- 2,3- 5,7- 5,8- and 6,7-dimethyltetralins; (3) the dehydrogenation of the dimethyltetralin(s) to form the corresponding dimethylnaphthalene(s), and (4) the isomerization of the resulting dimethylnaphthalene(s) to the desired specific dimethylnaphthalene. The 1,5-, 1,6-, and 2,6-dimethylnaphthalenes make up the group that is commonly referred to as the Group A triad. The 1,7-, 1,8- and 2,7-dimethylnaphthalenes make up the group that is commonly referred to as the Group B triad. The 1,3-, 1,4- and 2,3-dimethylnaphthalenes make up the group that is commonly referred to as the Group C triad. In this regard, it is known that in the presence of an acid catalyst, the dimethylnaphthalene isomers are isomerizable within each triad of dimethylnaphthalene isomers—that is, within the 1,5- 1,6- and 2,6-dimethylnaphthalenes of triad A, within the 1,7- 1,8-, and 2,7-dimethylnaphthalenes of triad B, and within the 1,3-, 1,4- and 2,3-dimethylnaphthalenes of triad C. It is also known that the interconversion of a dimethylnaphthalene isomer within one of the aforesaid triads to a dimethylnaphthalene isomer within another of the aforesaid triads occurs to a relatively lesser extent.

For example, Sikkenga et al., U.S. patent application Ser. No. 316,308 filed Feb. 27, 1989, discloses an improved method for preparing one or more dimethyltetralins from 5-(o-, m-, or p-tolyl)-pent-1- or -2-ene or 5-phenyl-hex-1- or -2-ene as the first feedstock which comprises contacting the first feedstock in liquid form with solid cyclization catalyst comprising an acidic, ultrastable crystalline aluminosilicate molecular sieve Y-zeolite that is substantially free of adsorbed water, and at a temperature in the range of from about 120° C. to about 350° C. at a pressure that is sufficiently high to maintain the first feedstock substantially in the liquid phase to thereby cyclize the first feedstock to form a first liquid product comprising one or more dimethyltetralins, wherein water is at a concentration in the first feedstock of from 0.0 up to less than about 0.5 weight percent, based on the weight of the feedstock, wherein (a) when the first feedstock comprises 5-(o-tolyl)-pent-1- or -2-ene, at least 80 weight percent of the dimethyltetralin product formed is comprised of 1,5-, 1,6-, 2,5- or 2,6-dimethyltetralin or a mixture thereof, (b) when the first feedstock comprises 5-(m-tolyl)-pent-1- or -2-ene, at least 80 weight percent of the mixture of the dimethyltetralin product formed is comprised of 1,5- 1,6- 1,7- 1,8- 2,5-, 2,6-, 2,7- or 2,8-dimethyltetralin or a mixture thereof, (c) when the first feedstock comprises 5-(p-tolyl)-pent-1- or 2-ene, at least 80 weight percent of the dimethyltetralin product formed is comprised of 1,7-, 1,8-, 2,7- or 2,8-dimethyltetralin or a mixture thereof, and (d) when the first feedstock comprises 5-phenyl-1- or -2-hexene, at least 80 weight percent of the dimethyltetralin product formed is comprised of 1,3-, 1,4-, 2,3-, 5,7-, 5,8- or 6,7-dimethyltetralin or a mixture thereof.

Thompson, U.S. Pat. Nos. 3,775,496; 3,775,497; 3,775,498; and 3,775,500 disclose processes for the cyclization of specific alkenylbenzenes to one or more specific dimethyltetralins at 200°–450° C. in the presence of any suitable solid acidic cyclization catalyst such as acidic crystalline zeolites as well as silica-alumina, silica-magnesia, and silica-alumina-zirconia and phosphoric acid, followed by the dehydrogenation of the resulting dimethyltetralin(s) in the vapor state to the corresponding dimethylnaphthalene(s) in a hydrogen atmosphere at 300°–500° C. and in the presence of a solid dehydrogenation catalyst such as noble metals on carriers and chromia-alumina, and thereafter isomerization of each of the aforesaid dimethylnaphthalene(s) to the desired isomer within the triad of dimethylnaphthalenes to which the isomer being isomerized belongs at 275°–500° C. in the presence of a solid acidic isomerization catalyst of the same type as described in respect of the cyclization disclosed therein. In the alternative, both the cyclization and isomerization reactions can be performed in the liquid phase, in which case the cyclization is performed at 200°–275° C. with a solid phosphoric acid catalyst, at 70°–140° C. with an acidic ion exchange resin, an acidic crystalline zeolite, hydrofluoric or sulfuric acid as the catalyst or a siliceous cracking catalyst.

More specifically, Thompson, U.S. Pat. No. 3,775,496, discloses the cyclization of 5-(m-tolyl)-pent-2-ene to 1,6- and 1,8-dimethyltetralins, which are then dehydrogenated to 1,6- and 1,8-dimethylnaphthalenes, which in turn are isomerized to 2,6- and 2,7-dimethylnaphthalenes, respectively. Thompson, U.S. Pat. No.

3,775,497, discloses the cyclization of 5-phenyl-hex-2-ene to 1,4-dimethyltetralin which is then dehydrogenated to 1,4-dimethylnaphthalene, which is in turn isomerized to 2,3-dimethylnaphthalene. Thompson, U.S. Pat. No. 3,775,498, discloses the cyclization of 5-(o-tolyl)-pent-2-ene to 1,5-dimethyltetralin, which is then dehydrogenated to 1,5-dimethylnaphthalene, which is in turn isomerized to 2,6-dimethylnaphthalene. Thompson, U.S. Pat. No. 3,775,500 discloses the cyclization of 5-(p-tolyl)-pent-2-ene to 1,7-dimethyltetralin, which is then dehydrogenated to 1,7-dimethylnaphthalene, which in turn is isomerized to 2,7-dimethylnaphthalene.

A problem in all such prior art methods is the presence as impurities of other dimethylnaphthalene isomers and unconverted dimethyltetralin and alkenylbenzene as well as by-products produced in the akenylation, cyclization and dehydrogenation steps, that are present with the finally obtained, desired specific dimethylnaphthalene isomer. The presence of such impurities and by-products markedly reduces the utility and commercial value of the desired dimethylnaphthalene isomer, especially as a precursor for the formation of a naphthalene dicarboxylic acid for use as a monomer in the manufacture of a polymer. In particular, as indicated hereinabove, both Thompson, U.S. Pat. Nos. 3,775,496 and 3,775,498, disclose that $C_{24}$ dimeric alkylation by-products may be formed in the cyclization step and that these by-products are reconverted to $C_{12}$ material including dimethylnaphthalenes when the cyclization product mixture is dehydrogenated. In addition, catalysts tend to deactive relatively rapidly at the high temperatures typically employed in vapor phase processes or even in liquid phase processes. Therefore, it is highly desirable to employ relatively lower temperature liquid phase processes and to improve the completeness of each step in the aforesaid multistep synthesis and the selectivity of each step therein for the production of the desired product therefrom.

Consequently, it is highly desired to improve the selectivity of the cyclization step in the aforesaid multistep synthesis for the formation of dimethyltetralin isomers which upon dehydrogenation are converted to dimethylnaphthalene isomers that belong to the same triad to which also belongs the specific desired dimethylnaphthalene isomer. Improved selectivity of the cyclization step and elimination of undesirable cyclization by-products from the feed to the dehydrogenation step also improves the selectivities of the subsequent dehydrogenation and isomerization steps.

OBJECTS OF THE INVENTION

It is therefore a general object of the present invention to provide an improved method for manufacturing with an improved yield and selectivity, a specific dimethyltetralin isomer or set of dimethyltetralin isomers by the cyclization of an alkenybenzene which meets the aforementioned requirements for selectivity and completeness and catalyst activity.

It is a related object of the present invention to provide an improved method for manufacturing with an improved yield and selectivity, a specific dimethyltetralin isomer or set of dimethyltetralin isomers by providing an improved cyclization of an alkenylbenzene to form a specific dimethyltetralin isomer or set of dimethyltetralin isomers with an increased selectivity and improved catalyst activity and further eliminating undesirable, relatively heavier by-products from the cyclization product mixture.

Other objects and advantages of the method of the present invention will become apparent upon reading the following detailed description and appended claims.

SUMMARY OF THE INVENTION

The objects of the invention are achieved by an improved method for preparing one or more dimethyltetralins from 5-(o-, m-, or p-tolyl)-pent-1- or -2-ene or 5-phenyl-hex-1- or -2-ene as the first feedstock, comprising: (a) contacting the first feedstock in liquid form with a solid cyclization catalyst comprising an acidic crystalline aluminosilicate molecular sieve Y-zeolite that is substantially free of absorbed water, at a temperature in the range of from about 120° C. to about 350° C. at a pressure that is sufficiently high to maintain the feedstock substantially in the liquid phase to thereby cyclize the first feedstock to form a liquid product comprising one or more dimethyltetralins, wherein water is at a concentration in the feedstock of from 0.0 up to less than about 0.5 weight percent, based on the weight of the feedstock, wherein (1) when the first feedstock comprises 5-(o-tolyl)-pent-1- or -2-ene, at least 80 weight percent of the dimethyltetralin product formed is comprised of 1,5-, 1,6-, 2,5- or 2,6-dimethyltetralin, (2) when the first feedstock comprises 5-(m-tolyl)-pent-1- or -2-ene, at least 80 weight percent of the dimethyltetralin product formed is comprised of 1,5-, 1,6-, 1,7-, 1,8-, 2,5-, 2,6-, 2,7- or 2,8-dimethyltetralin or a mixture thereof, (3) when the first feedstock comprises 5-(p-tolyl)-pent-1- or -2-ene, at least 80 weight percent of the dimethyltetralin product formed is comprised of 1,7-, 1,8-, 2,7- or 2,8-dimethyltetralin or a mixture thereof, and (4) when first feedstock comprises 5-phenyl-1- or -2-hexene, at least 80 weight percent of the dimethyltetralin product formed is comprised of 1,3-, 1,4-, 2,3-, 5,7-, 5,8- or 6,7-dimethyltetralin or a mixture thereof; (b) separating the resulting cyclization product mixture by distillation at reduced pressure such that a lighter fraction comprising the dimethyltetralin product is separated as the overhead from a heaver fraction comprising materials boiling above the dimethyltetralins; and (c) combining the resulting heavier fraction with a fresh supply of the tolylpentene(s) or phenyl-hexene(s) employed in step (a) and cyclizing the resulting mixture under the cyclization conditions recited in step (a).

DETAILED DESCRIPTION OF THE PREFERRED EMBODIMENTS

Suitable feedstocks for use in the cyclization of the method of the present invention are 5-(o-, m-, or p-tolyl)-pent-1- or -2-ene or 5-phenyl-hex-1- or -2-ene. In the typical context in which the method of the present invention is employed, the dimethyltetralin product of the cyclization method of this invention is subsequently dehydrogenated to form one or more dimethylnaphthalenes which are then isomerized to the desired dimethylnaphthalene.

When 5-(o-tolyl)-pent-1- or -2-ene is the feedstock to the cyclization step of the present invention, 1,5-, 1,6-, 2,5-, or 2,6-dimethyltetralin or a mixture thereof comprises at least 80, preferably at least 85, weight percent of the dimethyltetralin product produced therefrom, which resulting dimethyltetralin product is in turn the feedstock and is converted in the aforesaid dehydrogenation step to the corresponding 1,5- 1,6- and 2,6-dimethylnaphthalenes, which are then the feedstock in the aforesaid isomerization step, wherein 1,5- and 1,6-dimethylnaphthalene therein are substantially converted to 2,6-dimethylnaphthalene.

When 5-(m-tolyl)-pent-1- or -2-ene is the feedstock to the cyclization step of the method of this invention, 1,5- 1,6- 1,7-, 1,8- 2,5- 2,6-, 2,7- or 2,8-dimethyltetralin or a mixture thereof comprises at least 80, preferably at least 85, weight percent of the dimethyltetralin product produced therefrom, which dimethyltetralins are in turn the feedstock and are converted in the aforesaid dehydrogenation step to the corresponding 1,5-, 1,6-, 1,7-, 1,8- 2,6- and 2,7-dimethylnaphthalenes, which are then the feedstock in the aforesaid isomerization step, wherein the 1,5-, 1,6-, 1,7- and 1,8-dimethylnaphthalenes therein are substantially converted to 2,6- and 2,7-dimethylnaphthalenes.

When 5-(p-tolyl)-pent-1- or -2-ene is the feedstock to the cyclization step of the method of this invention, 1,7-, 1,8-, 2,7- or 2,8-dimethyltetralin or a mixture thereof comprises at least 80, preferably at least 85, weight percent of the dimethyltetralin product produced therefrom, which dimethyltetralins are in turn the feedstock and are converted in the aforesaid dehydrogenation step to the corresponding 1,7-, 1,8- and 2,7-dimethylnaphthalenes, which are then the feedstock in the aforesaid isomerization step, wherein the 1,7- and 1,8-dimethylnaphthalenes therein are substantially converted to 2,7-dimethylnaphthalene.

When 5-phenyl-1- or -2-hexene is the feedstock to the cyclization step of the method of this invention, 1,3-, 1,4-, 2,3-, 5,7-, 5,8-, or 6,7-dimethyltetralin or a mixture thereof comprises at least 80, preferably at least 85, weight percent of the dimethyltetralin product produced therefrom, which dimethyltetralins are in turn the feedstock and are converted in the aforesaid dehydrogenation step to the corresponding, 1,3-, 1,4- and 2,3-dimethylnaphthalenes, which are then the feedstock in the aforesaid isomerization step, wherein the 1,3- and 1,4-dimethylnaphthalenes therein are substantially converted to 2,3-dimethylnaphthalene.

In the cyclization method of the present invention, the reaction is performed in the liquid phase at an elevated temperature and at a sufficiently high pressure to ensure that the feedstock is maintained substantially in the liquid phase. The cyclization reaction is performed at a temperature in the range of from about 120° C., preferably from about 150° C., to about 350° C., preferably to about 250° C., and generally at a pressure in the range of from about 0.05, preferably from about 0.1 to about 10, preferably to about 1.3 atmospheres absolute.

The cyclization reaction can be performed with or without a solvent for the feedstock. Preferably a solvent is not employed. If employed, a solvent must be inert under the conditions employed and suitably comprises a paraffin, such as a tetradecane, or an aromatic hydrocarbon, such as a anthracene, or mixtures thereof, which preferably boil above about 270° C. In the cyclization step, if water is present, its concentration must be less than 0.5 weight percent, preferably less than 0.1 weight percent, based on the weight of the alkenylbenzene feedstock. More preferably, water is not present in the cyclization reaction medium.

The cyclization method of the present invention can be performed either batchwise or continuously. The reaction apparatus to be used in either case can be of any known type such as a fixed bed, moving bed, fluidized bed, liquid phase suspended bed or a solid-liquid mixture in a stirred tank. Generally, however, the use of a fixed bed is commercially preferred for continuous operation.

The improved conversion of the feedstock and selectivity for the production of the desired product or set of products permit the use of less severe conditions—that is, lower temperatures and pressures—for the cyclization method of this invention such that greater selectivity and reduced catalyst deactivation can be achieved.

The catalyst employed in the cyclization method of this invention comprises an acidic, ultrastable—that is, a thermally stabilized or dealuminated—crystalline aluminosilicate Y-zeolite having a silica-to-alumina bulk molar ratio in the range of from about 3:1, preferably from about 12:1, to about 200:1, preferably to about 100:1, having pore windows provided by twelve-membered rings containing oxygen and a unit cell size in the range of from about 24.0, preferably from about 24.1, to about 24.7, preferably to about 24.3 angstroms, having a sodium content of from about 0.01 to about 0.4 weight percent, calculated as elemental sodium and based on the weight of the zeolite, and or reported in terms of the sodium oxide-to-alumina bulk molar ratio of from about 0.001:1 to about 1:1.

The term "relatively low acidity" as used herein in reference to a zeolite useful for the practice of this invention has reference to the relatively few Bronsted acid sites in the crystalline zeolite framework that provide sufficient acidity to catalyze the desired cyclization but without the production of undesirably large amounts of by-products. Substances that owe their acidity to the presence of protons are termed Bronsted acids. In the case of crystalline aluminosilicates or zeolites, a Bronsted acid site occurs in the crystalline zeolite framework where an aluminum atom surrounded by four oxygen atoms is present. Inasmuch as some of such Bronsted acid sites are neutralized by alkali metal present in the crystalline framework, the Bronsted acidity of a particular zeolite can be delineated by specifying the bulk molar ratios of silica-to-alumina and sodium oxide-to-alumina as set forth herein. In terms of the number of framework Bronsted acid sites per unit cell of the crystalline zeolite catalyst, for the purposes of the present method the catalyst has an average of no more than 10 framework Bronsted acid sites, preferably no more than about 4 such sites, per unit cell.

The term "ultrastable" as used herein in reference to a zeolite has reference to a zeolite which has been thermally stabilized or dealuminated to produce a synthetic zeolite having much improved resistance to degradation under acid and hydrothermal conditions. The term "zeolite Y" as used herein in reference to the contemplated crystalline aluminosilicate molecular sieve has reference to a zeolite which has the characteristic framework structure of the faujasite mineral class. The term "bulk molar ratio" as used herein denotes the molar ratio of the designated moieties regardless of whether present in the crystalline framework of the molecular sieve or not.

One type of catalyst that is suitable for use in the method of this invention as the cyclization catalyst and/or the cracking catalyst (as discussed hereinbelow) and that is disclosed in the aforesaid Sikkenga et al., patent application Ser. No. 316,308 is an acidic, ultrastable Y zeolite catalyst in the hydrogen form having a unit cell size in the range of from about 24.2 to about 24.7 Anstroms, a silica-to-alumina bulk molar ratio in the range of from about 4:1 to about 10:1 and a sodium content of from about 0.05 to about 3.5 weight percent, calculated as elemental sodium. Commercially available examples of this type of catalyst are LZ-Y72 and LZ-Y20, both marketed by UOP and both in powder form. In one embodiment, this zeolite optionally contains from about 0.01, more preferably from about 0.05, to about 3.0, preferably to about 1.5, weight percent of a component comprising a first metal selected from the group consisting of platinum, palladium, iridium and rhodium, calculated as the elemental metal and based on the weight of the catalyst. Suitably, this metal component comprises platinum. In this same embodiment, the catalyst can optionally also contain from about 0.01, preferably from about 1, to about 5, preferably to about 3, weight percent of a component comprising a second metal selected from the group consisting of copper, tin, gold, lead and silver, calculated as the elemental metal and based on the weight of the catalyst. Suitably, this second metal component comprises copper, tin or gold.

A preferred type of catalyst for use as the cyclization catalyst and/or the cracking catalyst in the method of this invention is another ultrastable zeolite Y in the hydrogen form and having a relatively low acidity that has relatively lower alumina and sodium oxide contents. The catalyst framework alumina concentration for such zeolite is indicated in part by the unit cell size which, as measured by x-ray diffraction, is no more than 24.3 Angstroms. The silica-to-alumina bulk molar ratio is at least about 12:1 and preferably at least about 30:1. The sodium oxide-to-alumina bulk molar ratio is in the range of from about 0.001:1, preferably from about 0.01:1, to about 1:1, preferably to about 0.05:1. The sodium content of this zeolite is less than about 0.4, preferably less than about 0.23 weight percent, based on the weight of the zeolite and calculated as elemental sodium. Commercially available examples of this type of preferred zeolite are Conteka CBV 760 from Conteka Company, Leiden, the Netherlands, and Valfor CP 301-26 from PQ Corporation, Valley Forge, Pa. Conteka CBV 760 has a sodium oxide-to-alumina bulk molar ratio of about 0.05:1, a silica-to-alumina bulk molar ratio of about 50:1, and a sodium content of about 0.08 weight percent based on the weight of the zeolite and calculated as elemental sodium, has a unit cell size of 24.2 Angstroms and a specific surface area of 720 square meters per gram, and is in powder form. Valfor CP 301-26 has a sodium oxide-to-alumina bulk molar ratio of about 0.02:1, a silica-to-alumina bulk molar ratio of about 80:1, a sodium content of about 0.02 weight percent based on the weight of the zeolite and calculated as elemental sodium, a unit cell size of 24.25 Angstroms, and a specific surface area of about 775 square meters per gram, and is also in powder form.

The zeolite catalyst used in the method of the present invention can be either in a powdered form or in a granular form. A powdered catalyst is conveniently mechanically dispersed by mixing action in the liquid phase reactant employed. When in a granular form, the granule size can vary widely, such as from about 0.03-inch to about 1 inch in average maximum diameter, the exact size in any given instance being influenced by the choice of particular fixed-bed reactor wherein the granular form is to be employed and through which the liquid phase reactant is circulated. As used herein, the term "granular form" is generic to porous structures having the various possible physical shapes, and made by the various possible physical shapes, and made by the various possible preparation methods, including compacting, extruding, and the like, and such term is inclusive of both supported and unsupported zeolite catalyst forms.

The aforesaid zeolite can be employed either unsupported or supported on a porous refractory, inorganic oxide that is inert under the conditions employed, such as silica, alumina, silica-alumina, magnesia, bentonite or other such clays. If a support is employed, preferably the support comprises silica, alumina, or silica-alumina. When a support is employed, the zeolite comprises from about 10, preferably from about 20, to about 90, preferably to about 80, weight percent based on the weight of the catalyst.

The zeolite is preferably substantially free of adsorbed water. If present on the zeolite, the adsorbed water can be removed from the zeolite by heating it in a dry atmosphere at about 250° C. for 0.5-1 hour. In the alternative, and less preferably, the presence of adsorbed water at a concentration of up to 15 weight percent of the catalyst can be tolerated if a reaction temperature of at least about 180° C. is employed.

If the cyclization is performed on a batch basis, the catalyst is employed such that the zeolite component therein is at a level in the range of from about 0.1, preferably from about 0.5, to about 5, preferably to about 3 weight percent of the weight of the alkenylbenzene feedstock, and the reaction time is from about 0.5, preferably from about 2, to about 10, preferably to about 6 hours. If the cyclization is performed on a continuous basis, the space velocity is in the range of from about 0.1, preferably from about 1, to about 100, preferably to about 50, parts of alkenylbenzene feedstock per part of zeolite component of the catalyst by weight per hour.

Under conditions at which the cyclization reaction is substantially complete, the resulting cyclization product mixture is separated by distillation at reduced pressure into a relatively lighter (or lower boiling) fraction that contains the dimethyltetralin product and a relatively heavier (or higher boiling) fraction that boils above the boiling point(s) of the dimethyltetralin product. The reduced pressure is preferably in the range of from about 0.03 up to less than about 1.0 atmosphere. The heavier fraction boils preferably above 240° C. and more preferably above 250° C. at atmospheric pressure. In a preferred embodiment of the method of this invention, either immediately after the cyclization or at least ultimately, the lighter fraction which is the distillate is dehydrogenated such that the dimethyltetralins therein are converted to the corresponding dimethylnaphthalenes.

The heavier fraction of the cyclization product mixture, which is the distillation bottom, remains in the cyclization reactor or is recycled to it, and is next combined with a fresh supply of the tolyl-pentene(s) or phenyl-hexene(s) employed as the feedstock in the aforesaid cyclization step, and the resulting mixture is subjected to the aforesaid cyclization conditions. Under conditions at which the cyclization reaction is substantially complete, the resulting cyclization product mixture is separated by distillation at reduced pressure into a relatively lighter (or lower boiling) fraction that contains the dimethyltetralin product and a relatively heavier (or higher boiling) fraction that boils above the boiling points of the dimethyltetralin product. The reduced pressure is preferably in the range of from about 0.03 up to about 1.0 atmosphere. The heavier fraction boils preferably above 240° C. and more preferably above 250° C. at atmospheric pressure. In a preferred embodiment of the method of this invention, either immediately after the cyclization or at least ultimately, the lighter fraction, which is the distillate, is dehydrogenated such that the dimethyltetralin(s) therein are converted to the corresponding dimethylnaphthalenes. Again, the heavier fraction of the cyclization product mixture, which generally is the distillation bottoms, remains in the cyclization reactor or is recycled to it, and is combined with a fresh supply of the tolyl-pentene(s) or phenyl-hexene(s) employed as the feedstock in the aforesaid cyclization step, and the resulting mixture is subjected to the aforesaid cyclization conditions. In a batch operation, the heavier fraction and fresh supply of tolyl-pentene(s) or phenyl-hexene(s) are combined at a ratio of from about 0.01 part, preferably from about 0.05 part, to about 2, preferably to about 0.35 parts, by weight of the heavier fraction per part of the aforesaid fresh supply. In a continuous operation, the heavier fraction and the fresh supply of tolyl-pentene(s) or phenyl-hexane(s) are combined at a ratio of from about 0.2 part, preferably from about 1 part to about 20 parts, preferably to about 5 parts by weight of the heavier fraction per part of fresh supply.

This sequence of cyclization of a mixture of fresh tolyl-pentene(s) or phenyl-hexene(s) and the distillation bottoms of the reduced pressure distillation of the products or the previous cyclization run, followed by reduced pressure distillation of the resulting cyclization products and combination of the resulting distillation bottoms with fresh tolyl-pentene(s) or phenyl-hexene(s) can be repeated until the activity of the cyclization catalyst declines to such an extent that the reaction times become excessive. Typically, in a batch operation this sequence of cyclization, separation and recycle of the distillation bottoms to the cyclization step is repeated up to 100 times, preferably from 5 to 30 times for a given charge of catalyst. Typically, in a continuous operation, relatively small amounts of the catalyst would be removed from the reactor and replaced in the reactor with fresh catalyst in order to maintain the desired catalyst activity.

At the end of a continuous cyclization run or at the end of a series of batch cyclization runs, the distillation bottoms from the last reduced pressure distillation can be subjected to cracking at a temperature in the range of from about 120° C., preferably from about 180° C., to about 450° C., preferably to about 330° C., which temperature is higher than the temperature at which the cyclization was performed by at least 10° C., preferably by at least 30° C. The cracking operation is performed at a pressure that is sufficiently high so that the materials being cracked are substantially in the liquid phase, and generally the pressure is from about 0.03, preferably from about 0.1, to about 10, preferably to about 2.0, atmospheres absolute. The cracking operation can be performed using as the cracking catalyst the same catalyst that had been employed as the cyclization catalyst. In the alternative, suitable cracking catalysts include any catalyst that is conventionally employed for acid-catalyzed reactions, such as silica-alumina, acidic molecular sieves, mineral acids or acidic ion exchange resins.

The resulting cracked products include dimethyltetralins which are then separated by distillation at a reduced pressure in the range of from about 0.03 to less than about 1.0 atmosphere into a lighter (or lower boiling) fraction which contains the dimethyltetralin product and a relatively heavier (or higher boiling) fraction that boils above the boiling point(s) of the dimethyltetralin product. In a preferred embodiment of the method of this invention either immediately after the cracking treatment or at least ultimately, the lighter fraction which is the distillate is dehydrogenated to convert the demethyltetralins therein to dimethylnaphthalenes. Thus, cracking the distillate bottoms from the last cyclization enhances the degree of the conversion of the tolyl-pentene(s) or phenyl-hexene(s) to dimethyltetralins, and, after the combination of cyclization, distillation and dehydrogenation steps of dimethylnaphthalenes. Similarly, the heavy cracked products which remain as the distillate bottoms after the combination of cyclization and distillation steps represent only a minor fraction of the total amount of comparably heavy materials that would have been produced in an equal number of cyclization runs in accordance with the method of aforesaid Sikkenga et al., U.S. patent application Ser. No. 316,308, and without subjecting the heavy cyclization products to further treatment in accordance with the method of this invention. Thus, the method of this invention produces greater relative amounts of useful dimethylnaphthalenes and produces a cyclization product mixture distillate as feedstock for subsequent dehydrogenation, which distillate contains substantially smaller amounts of relatively heavier cyclization products which have an adverse effect on the selectivities of the subsequent dehydrogenation and isomerization steps.

The present invention will be more clearly understood from the following specific examples.

EXAMPLE I

In Example I, 32 parts by weight of crude 1,5-dimethyltetralin (1,5-DMT) and 0.96 parts by weight of UOP's LZ-Y72 catalyst were introduced into a reactor, and the contents of the reactor were heated in the first run to the desired reaction temperature of 182° C., and 5-o-tolyl-pentene-2 (OTP) is introduced into the reactor slowly over a 2-hour period in order to allow removal of the exothermal heat and maintenance of good temperature control. A total of 48 parts of 5-o-tolyl-pentene-2 was added. The pressure was adjusted so as to maintain the reactants at their boiling point in the liquid phase. When the cyclization reaction was substantially complete and at least 99 weight percent of the 5-o-tolyl-pentene-2 had reacted, the reactor pressure was reduced to 2-4 psia. and the dimethyltetralin components of the product mixture were removed by low pressure distillation. The higher boiling materials and catalyst remained in the reactor as residue from the first run.

In the second run, the procedure of the first run was repeated, except that the higher boiling residue from the previous run was used instead of the crude 1,5-DMT and no additional catalyst was introduced. In each of the third, fourth and fifth runs, the procedure of the second run was repeated. The overall combined composition of the feedstocks employed in the five runs is indicated in Table I. The lower boiling products withdrawn as distillates in the five runs were combined, and the composition of this combination is also indicated in Table I. The higher boiling product remaining in the reactor as residue from the fifth run was analyzed, and its composition is also reported in Table I. This residue from the fifth run and distillation was then subjected to cracking under the same conditions and treatment employed in the fifth run, except that a reaction temperature of 250°–260° C. was employed and no 5-o-tolyl-pentene-2 was added. The cracked products boiling below the cracking temperature were removed by low pressure distillation as the "final distillate," and its composition is reported in Table I. The higher boiling products remained in the reactor as the "final residue.", and its composition is also reported in Table I. The overall composition of the total of the distillates from the five runs and the final distillate from the fifth distillation residue is reported in Table I as the combined 6 Distillates.

The results of Example I illustrate clearly that the distillation overhead which contains the dimethyltetralins (DMTs) and serves as the feedstock for the subsequent dehydrogenation to form dimethylnaphthalenes (DMNs) contains essentially no detectable heavies. Also, since the cyclization catalyst is not separated from the heavy distillation bottoms and is recycled to the cyclization step with this heavy fraction, there are no losses of catalyst due to filtration or other separation of the catalyst. The cracking step also reduces the total amount of unuseful distillation residue from 5.11 weight percent to 1.25 weight percent of the total product and therefore increases the absolute amount of useful DMTs and DMNs produced in the cyclization reaction.

solid cyclization catalyst was added to this heel, and the reactor was heated under reduced pressure to obtain reflux at the desired reaction temperature in the liquid state. A portion of 5-o-tolyl-pentene-2 was then gradually added to the reaction mixture over a period of 2 hours to allow removal of the exothermic heat and maintenance of good temperature control. Unlike Example 2, at the end of the reaction time—that is, when at least 99 weight percent of the 5-o-tolyl-pentene-2 has reacted—as indicated by gas chromatographic analysis, the pressure is slowly reduced to 2.4 pounds per square inch absolute, and slowly the temperature was decreased to below the reaction temperature in order to flash distill the lighter or lower boiling fraction containing the dimethyltetralin products. The products that distilled were collected outside the reactor and analyzed. The solid catalyst and heavy products remaining in the reactor constituted approximately 25 weight percent of total cyclization product mixture. The heavy products and catalyst remaining in the reactor served as the heel for the next run, as described below.

In each of Examples 4–9, to the heel (including the catalyst) from the previous example, using the proce-

TABLE 1

| | | | | Composition | | |
|---|---|---|---|---|---|---|
| | | | | | Products from Cracking and Distillation of 5th Distillation Residue | |
| | | | 5th | | | |
| Components | Combined 5 Feedstocks | Combined 5 Distillates | Distillation Residue | Final Distillate | Final Residue | Combined 6 Distillates |
| OTP | 88.59 | 1.37 | 0 | 0 | 0 | 1.3 |
| Saturated OTP | 0.56 | 4.10 | 0 | 6.60 | 0 | 4.2 |
| Unknown DMT | 0.16 | 1.29 | 0 | 5.10 | 0 | 1.4 |
| 1,6-DMT | 0.27 | 3.20 | 0.28 | 10.80 | 0 | 3.5 |
| 2,5-DMT | 0.06 | 1.40 | 0.26 | 8.6 | 0 | 1.7 |
| 1,5-DMT | 9.54 | 83.81 | 11.1 | 8.9 | 0 | 80.9 |
| 1,6-DMN | 0.03 | 0.41 | 0.36 | 3.3 | 0 | 0.5 |
| 1,5-DMN | 0.28 | 1.87 | 1.67 | 0.9 | 0 | 1.9 |
| Heavies | 0.51 | 0.06 | 83.5 | 1.00 | 100.0 | 0.1 |
| Other | 0.30 | 2.49 | 2.83 | 54.76 | 0 | 4.5 |
| Total useful DMTs and DMNs | 10.18 | 90.69 | 13.67 | 32.54 | 0 | 88.5 |
| Total | 100.00 | 100.00 | 100.00 | 100.00 | 100.00 | 100.00 |
| Percent of total product | — | 94.89 | 5.11 | 3.86 | 1.25 | 98.75 |

EXAMPLES 2–9

Each of Examples 2–9 was performed batchwise. In Example 2, 150 grams of 5-o-tolyl-pentene-2 and 1.80 grams of the particular solid cyclization catalysts employed were charged to a reactor equipped with a reflux condenser and distillation/collection head, and the reactor was evacuated to the desired reaction pressure. The reactor contents were then heated to the reaction temperature, at which point the reactor contents were at reflux. The pressure was controlled to maintain the reactants in the liquid phase. When at least 99 weight percent of the 5-o-tolyl-pentene-2 was converted, as indicated by gas chromatographic measurement, the reaction time was noted, and the temperature of the reactor contents was gradually reduced, and the pressure was gradually increased to atmospheric pressure. No product was distilled out of or removed from the reactor. When cooled, the reactor contents included the cyclization product mixture and solid catalyst employed, and a 1.8 gm sample of the product mixture was withdrawn for analysis.

In Example 3, the entire product mixture and catalyst from Example 2 was returned to the reactor as the heel for the next batch of 5-o-tolyl-pentene-2. Additional dure of Example 3, a portion of 5-o-tolyl-pentene-2, but no additional solid catalyst was added, and the reactor contents were heated and maintained under vacuum to allow reflux. At the completion of the cyclization reaction, the reactor pressure was reduced further, and the lighter products were flash distilled, collected and analyzed, and the heavy products and catalyst remaining in the reactor were employed as the heel for the next run (Example), also as described for Example 3. The catalyst employed in Examples 2–9 was Conteka CBV 760.

The conditions employed and results from Examples 2–9 are presented in Tables 2–3.

EXAMPLES 10–17

Example 10 was performed using the same general procedure employed in Example 2 and the product mixture produced in Example 10 served as the heel for Example 11. Examples 11–17 were performed using the same general procedures of Examples 3–9. The catalyst employed in Examples 10–17 was UOP's LZ-Y72. The conditions employed in, and the results from, Examples 10–17 are presented in Tables 4–5.

EXAMPLE 18

In Example 18 for the run on the first day of operation 8.83 grams of Conteka 760 catalyst and 440 grams of a liquid reaction medium were introduced into a 1000-milliliter stirred tank reactor which was maintained at the desired reaction temperature and which was fitted with the overhead distillation column connected to a vacuum system. The reactor pressure was reduced to 0.2 to 0.3 atmosphere in order to achieve reflux at the desired reaction temperature, and then liquid 5-0-tolyl-2-pentene (OTP) was passed continuously through the liquid reaction medium in the reactor, and reaction product passed continuously upward into the distillation column. The portion of the reaction product boiling below about 265° C. (at 1 atmosphere pressure) was continuously withdrawn as overhead from the distillation column, and the higher boiling fractions were either returned to the reactor as distillation bottoms or never vaporized or passed into the distillation column.

A run for a particular day was concluded by discontinuing the flow of OTP into the reactor, cooling the reactor contents to room temperature, raising the reactor pressure to one atmosphere while purging the reactor with nitrogen in order to eliminate oxygen. To begin the next day's run, the reactor was heated to the desired reaction temperature, reactor pressure was reduced to 0.2–0.3 atmosphere in order to bring the reactor contents to reflux and then liquid OTP was again passed into the reactor, and into the heavy liquid reaction product that boiled above 265° C. (at 1 atmosphere pressure) and that remained in the reactor from the previous day's run, but without the introduction of additional catalyst or liquid reaction medium.

TABLE 2

|  | Example 2 | Example 3 | Example 4 | Example 5 | Example 6 | Example 7 | Example 8 | Example 9 |
|---|---|---|---|---|---|---|---|---|
| Heel wt. (g) | — | 148.2 | 171.6 | 179.1 | 206.0 | 204.8 | 199.6 | 197.6 |
| Liquid Wt. (g) | — | 146.4 | 164.4 | 171.9 | 198.8 | 197.6 | 192.4 | 190.4 |
| Catalyst wt. (g) | — | 1.8 | 7.2 | 7.2 | 7.2 | 7.2 | 7.2 | 7.2 |
| OTP wt. (g) | 150 | 448 | 450 | 439 | 420 | 450 | 441 | 451 |
| Added catalyst wt. (g) | 1.8 | 5.4 | 0 | 0 | 0 | 0 | 0 | 0 |
| Total catalyst weight (g) | 1.8 | 7.2 | 7.2 | 7.2 | 7.2 | 7.2 | 7.2 | 7.2 |
| Reaction temperature (°C.) | 180 | 180 | 180 | 180 | 180 | 180 | 180 | 180–200 |
| Reaction pressure (psia) | 2–4 | 2–4 | 2–4 | 2–4 | 2–4 | 2–4 | 2–4 | 2–4 |
| Reaction time (hrs.) | 3 | <2 | <2 | <2 | <2 | <2 | <2 | <2 |
| Reduced pressure (psia) | — | 1–2 | 1–3 | 2–3 | 2–3 | 2–3 | 2–3 | 2–3 |
| Distilled product wt. (g) | 1.8* | 431.8 | 442.5 | 412.1 | 421.2 | 455.2 | 443.0 | 444.7 |
| Residual product wt. (g) | 148.2 | 164.4 | 171.9 | 198.8 | 197.6 | 192.4 | 190.4 | 186.7 |

*a 1.8 g sample of the undistilled total 148.2 g residual product reactor contents

TABLE 3

| | Composition of Distilled Product Removed From Reactor (Wt. %) | | | | | | | |
|---|---|---|---|---|---|---|---|---|
| | Example 2* | Example 3 | Example 4 | Example 5 | Example 6 | Example 7 | Example 8 | Example 9 |
| Components | | | | | | | | |
| OTP | 0.2 | 0.0 | 0.0 | 0.1 | 0.0 | 0.1 | 0.1 | 0.0 |
| saturated OTP | 1.9 | 3.1 | 2.0 | 2.0 | 2.2 | 1.8 | 2.1 | 2.2 |
| unknown DMT isomers | 0.5 | 0.5 | 0.4 | 0.4 | 0.4 | 0.4 | 0.4 | 0.5 |
| 2,6-, 2,7- and 1,7-DMT | 0.1 | 0.1 | 0.1 | 0.1 | 0.1 | 0.1 | 0.1 | 0.1 |
| 1,6-DMT | 0.5 | 0.5 | 0.7 | 0.7 | 0.8 | 0.7 | 0.7 | 1.0 |
| 2,8-DMT | 0.8 | 0.8 | 0.8 | 0.8 | 0.8 | 0.8 | 0.9 | 0.8 |
| 2,5-DMT | 0.1 | 0.2 | 0.3 | 0.3 | 0.4 | 0.3 | 0.3 | 0.4 |
| 1,5-DMT | 87.3 | 93.1 | 94.1 | 93.9 | 93.4 | 93.7 | 93.5 | 93.1 |
| 2,6-, 2,7-DMN | 0.0 | 0.0 | 0.0 | 0.0 | 0.0 | 0.0 | 0.0 | 0.0 |
| 1,7-DMN | 0.0 | 0.0 | 0.0 | 0.0 | 0.0 | 0.0 | 0.0 | 0.0 |
| 1,6-DMN | 0.0 | 0.0 | 0.0 | 0.0 | 0.1 | 0.1 | 0.1 | 0.1 |
| 1,5-DMN | 0.8 | 0.7 | 1.0 | 1.1 | 1.1 | 1.3 | 1.1 | 1.0 |
| 1,8-DMN | 0.0 | 0.0 | 0.0 | 0.0 | 0.0 | 0.0 | 0.0 | 0.0 |
| Heavies | 3.4 | 0.0 | 0.1 | 0.1 | 0.1 | 0.1 | 0.2 | 0.2 |
| Unknown | 2.5 | 0.2 | 0.2 | 0.2 | 0.2 | 0.2 | 0.2 | 0.2 |
| Total useful DMTs | 88.0 | 94.1 | 95.2 | 94.9 | 94.7 | 94.8 | 94.5 | 94.6 |
| Total useful DMNs | 0.8 | 0.7 | 1.0 | 1.1 | 1.1 | 1.3 | 1.1 | 1.0 |
| Total useful products | 88.8 | 94.8 | 96.2 | 96.0 | 95.8 | 96.1 | 95.6 | 95.6 |
| Total products | 100 | 100 | 100 | 100 | 100 | 100 | 100 | 100 |
| Parts of Distilled Products per 100 parts of OTP feedstock (including Ex 2) | | | | | | | | |
| Total useful products | — | 68.7 | 79.8 | 82.8 | 85.7 | 87.9 | 89.2 | 89.9 |
| Total major by-products | | | | | | | | |
| Saturated OTP | — | 2.2 | 2.1 | 2.0 | 2.1 | 2.0 | 2.0 | 2.1 |
| 2,7-Triad DMTs | — | 0.7 | 0.7 | 0.8 | 0.8 | 0.8 | 0.8 | 0.8 |
| Unknown DMT isomers | — | 0.4 | 0.4 | 0.4 | 0.4 | 0.4 | 0.4 | 0.4 |
| Unknowns | — | 0.1 | 0.1 | 0.1 | 0.2 | 0.2 | 0.2 | 0.2 |
| Heavies | — | 0.0 | 0.0 | 0.1 | 0.1 | 0.1 | 0.1 | 0.1 |

*the composition of the undistilled total reaction product remaining in the reactor

TABLE 4

|  | Example 10 | Example 11 | Example 12 | Example 13 | Example 14 | Example 15 | Example 16 | Example 17 |
|---|---|---|---|---|---|---|---|---|
| Heel wt. (g) | — | 149.0 | 156.7 | 142.5 | 194.6 | 181.6 | 187.6 | 202.3 |
| Liquid wt. (g) | — | 147.2 | 149.5 | 135.3 | 187.4 | 174.4 | 180.4 | 195.1 |
| Catalyst wt. (g) | — | 1.8 | 7.2 | 7.2 | 7.2 | 7.2 | 7.2 | 7.2 |
| OTP wt. (g) | 150 | 440 | 440 | 440 | 403 | 417 | 420.6 | 406.6 |
| Added catalyst wt. (g) | 1.8 | 5.4 | 0.0 | 0.0 | 0.0 | 0.0 | 0.0 | 0.0 |
| Total Catalyst weight (g) | 1.8 | 7.2 | 7.2 | 7.2 | 7.2 | 7.2 | 7.2 | 7.2 |
| Reaction temperature (°C.) | 190 | 190 | 200 | 216 | 237 | 238 | 238 | 238 |
| Reaction pressure (psia) | 4–5 | 4–5 | 5–6 | 10–12 | 14.7 | 14.7 | 14.7 | 14.7 |
| Reaction time (hrs.) | 4.5 | 4.0 | 7.0 | 8.0 | 2.8 | 2.8 | 2.8 | 2.8 |
| Reduced pressure (psia) | — | 1–2 | 1–2 | 1–2 | 1–2 | 1–2 | 1–2 | 1–2 |
| Distilled product wt. (g) | 2.8* | 437.7 | 454.2 | 387.9 | 415.6 | 411.4 | 405.6 | 391.4 |
| Residual product wt. (g) | 147.2 | 149.5 | 135.3 | 187.4 | 174.8 | 180.4 | 195.1 | 210.3 |

*a 2.8 g sample of the undistilled total 147.2 residual product reactor contents

TABLE 5

| | Composition of Distilled Products Removed from Reactor (wt. %) | | | | | | | |
|---|---|---|---|---|---|---|---|---|
| Components | Example 10* | Example 11 | Example 12 | Example 13 | Example 14 | Example 15 | Example 16 | Example 17 |
| o-xylene | 0.1 | 0.1 | 0.1 | 0.2 | 0.3 | 0.2 | 0.2 | 0.2 |
| OTP | 0.3 | 0.1 | 0.3 | 0.1 | 0.2 | 0.1 | 0.1 | 0.1 |
| saturated OTP | 2.5 | 4.4 | 2.8 | 3.9 | 5.0 | 4.9 | 4.7 | 4.7 |
| Unknown DMT isomers | 0.9 | 1.2 | 1.0 | 1.3 | 1.8 | 1.8 | 1.8 | 1.7 |
| 2,6-, 2,7-, 1,7-DMT | 0.2 | 0.2 | 0.2 | 0.3 | 0.5 | 0.4 | 0.4 | 0.4 |
| 1,6-DMT | 0.9 | 0.9 | 0.9 | 1.2 | 2.5 | 2.3 | 1.9 | 1.9 |
| 2,8-DMT | 0.8 | 0.9 | 0.9 | 0.8 | 0.8 | 0.8 | 0.9 | 0.9 |
| 2,5-DMT | 0.3 | 0.3 | 0.4 | 0.6 | 0.9 | 0.8 | 0.7 | 0.8 |
| 1,5-DMT | 85.8 | 90.0 | 89.8 | 89.0 | 84.6 | 85.3 | 86.1 | 86.4 |
| 2,6-, 2,7-DMN | 0.0 | 0.0 | 0.0 | 0.0 | 0.0 | 0.0 | 0.0 | 0.0 |
| 1,7-DMN | 0.0 | 0.0 | 0.0 | 0.0 | 0.0 | 0.0 | 0.0 | 0.0 |
| 1,6-DMN | 0.1 | 0.0 | 0.1 | 0.1 | 0.3 | 0.3 | 0.3 | 0.2 |
| 1,5-DMN | 1.3 | 1.1 | 1.6 | 1.6 | 2.2 | 2.2 | 2.2 | 2.0 |
| 1,8-DMN | 0.0 | 0.0 | 0.1 | 0.0 | 0.0 | 0.0 | 0.0 | 0.0 |
| Heavies | 4.6 | 0.0 | 0.1 | 0.0 | 0.0 | 0.0 | 0.1 | 0.0 |
| Unknown | 0.8 | 0.2 | 0.6 | 0.3 | 0.2 | 0.1 | 0.1 | 0.1 |
| Total useful DMTs | 86.9 | 91.2 | 91.1 | 90.7 | 88.1 | 87.5 | 88.7 | 89.0 |
| Total useful DMNs | 1.4 | 1.1 | 1.7 | 1.7 | 2.5 | 2.5 | 2.5 | 2.2 |
| Total useful products | 88.3 | 92.3 | 92.8 | 92.4 | 90.6 | 90.0 | 91.2 | 91.2 |
| Total products | 100 | 100 | 100 | 100 | 100 | 100 | 100 | 100 |
| Parts of Distilled Products per 100 parts of OTP feedstock (including Ex 10) | | | | | | | | |
| Total useful products | — | 68.2 | 79.6 | 79.9 | 82.7 | 83.8 | 84.4 | 84.8 |
| Total major by-products | | | | | | | | |
| Saturated OTP | — | 3.3 | 3.1 | 3.2 | 3.6 | 3.8 | 3.9 | 4.0 |
| 2,7-Triad DMTs | — | 0.8 | 1.0 | 1.0 | 1.1 | 1.1 | 1.1 | 1.1 |
| Unknown DMT isomers | — | 0.9 | 0.9 | 1.0 | 1.1 | 1.1 | 1.1 | 1.1 |
| Unknown | — | 0.1 | 0.4 | 0.3 | 0.3 | 0.3 | 0.2 | 0.2 |
| Heavies | — | 0.0 | 0.0 | 0.0 | 0.0 | 0.0 | 0.0 | 0.0 |

*the composition of the undistilled total reaction product remaining in the reactor

TABLE 6

| | | Day No. | | | | | | | | |
|---|---|---|---|---|---|---|---|---|---|---|
| | Initial Reaction Medium | 1 | 2 | 3 | 4 | 5 | 6 | 7 | 8 | Final Reaction Medium |
| Feed Rate (g/hr) | | 233 | 233 | 233 | 233 | 233 | 233 | 233 | 233 | |
| Catalyst Charge (g) | | 8.83 | 8.83 | 8.83 | 8.83 | 8.83 | 8.83 | 8.83 | 8.83 | |
| Average Temperature (C.) | | 200 | 200 | 200 | 200 | 200 | 200 | 210 | 210 | |
| Average Pressure (psia) | | 4.4 | 4.0 | 3.7 | 3.6 | 3.6 | 3.6 | 4.3 | 4.3 | |
| Hours on Feed for the Day (hrs.) | | 5.8 | 7.7 | 9.6 | 11.6 | 7.6 | 11.8 | 7.7 | 11.7 | |
| WHSV (g DTP/g cut-hr) | | 26.4 | 26.3 | 26.3 | 25.8 | 26.6 | 25.8 | 26.3 | 26.0 | |
| Wt. of Feed into the Reactor (g) | | 1349 | 1788 | 2235 | 2682 | 1788 | 2682 | 1788 | 2682 | |
| Reactor Contents (g) | 440 | 432 | 403 | 401 | 431 | 470 | 494 | 502 | 512 | 512 |
| Cumulative Conditions - End of Day | | | | | | | | | | |
| Hours on catalyst | | 5.8 | 13.5 | 23.1 | 34.9 | 42.5 | 54.3 | 62.0 | 73.7 | |

TABLE 6-continued

| | | | | | | | | |
|---|---|---|---|---|---|---|---|---|
| Wt. of Feed into Reactor[1] | 1781 | 3569 | 5804 | 8486 | 10274 | 12956 | 14744 | 17426 |
| Wt. Feed/Wt. Catalyst | 152 | 354 | 607 | 911 | 1113 | 1417 | 1619 | 1923 |
| Overhead Product Removed | 1359 | 3166 | 5403 | 8055 | 9804 | 12462 | 14242 | 16914 |

| | | Composition | | | | | | | | |
|---|---|---|---|---|---|---|---|---|---|---|
| Component | Initial Reaction Medium | \multicolumn{8}{c|}{Average Distillate for Day No.} | | Final Reaction Medium |
| | | 1 | 2 | 3 | 4 | 5 | 6 | 7 | 8 | |
| OTP | 1.7 | 0.1 | 0.2 | 0.4 | 0.6 | 0.7 | 0.9 | 1.0 | 0.9 | 0.0 |
| 2,6-Triad DMT's and DMN's | 92.8 | 93.9 | 94.9 | 94.8 | 94.6 | 94.5 | 94.3 | 93.7 | 93.8 | 58.9 |
| Sat'd OTP | 3.0 | 3.3 | 2.5 | 2.5 | 2.4 | 2.4 | 2.4 | 2.8 | 2.8 | 0.8 |
| 2,7-Triad DMT's | 0.9 | 1.2 | 1.1 | 1.1 | 1.1 | 1.1 | 1.1 | 1.1 | 1.1 | 0.5 |
| Heavies | 0.2 | 0.0 | 0.1 | 0.2 | 0.2 | 0.3 | 0.3 | 0.3 | 0.3 | 39.3 |

| | Cumulative Yield of Distillate Component Based on Total Reactor Charge After Day No. | | | | | | | |
|---|---|---|---|---|---|---|---|---|
| Component | 1 | 2 | 3 | 4 | 5 | 6 | 7 | 8 |
| OTP | 0.1 | 0.2 | 0.3 | 0.6 | 0.7 | 0.8 | 0.9 | 0.9 |
| 2,6-Triad DMTs and DMNs | 71.1 | 84.2 | 88.2 | 89.8 | 90.2 | 90.7 | 90.5 | 91.1 |
| Sat'd OTP | 2.5 | 2.2 | 2.3 | 2.3 | 2.3 | 2.3 | 2.7 | 2.7 |
| 2,7-Triad DMTs | 0.9 | 1.0 | 1.0 | 1.0 | 1.0 | 1.0 | 1.1 | 1.1 |
| Heavies | 0.0 | 0.1 | 0.2 | 0.2 | 0.3 | 0.3 | 0.3 | 0.3 |

The reaction conditions employed and the results from Example 18 are presented in Table 6.

From the above description, it is apparent that the objects of the present invention have been achieved. While only certain embodiments and various modifications will be apparent from the above description to those skilled in the art. These alternatives are considered equivalents and are within the spirit and scope of the present invention.

Having described the invention, what is claimed is:

1. A method for preparing one or more dimethyltetralins from 5-(o-,m-, or p-tolyl)-pent-1- or -2-ene or 5-phenyl-hex-1- or -2-ene, comprising:

(a) contacting a feedstock comprising 5-(o-, m-, or p-tolyl)-pent-1- or 2-ene or 5-phenyl-hex-1- or -2-ene in liquid form with a solid cyclization catalyst comprising an ultrastable, crystalline aluminosilicate molecular sieve Y-zeolite that is substantially free of absorbed water and having a silica-to-alumina bulk molar ratio in the range of about 3:1 to about 200:1, pore windows provided by twelve-membered rings containing oxygen, a unit cell size in the range of about 24.0 to about 24.7 Angstroms, and a sodium content of about 0.01 to about 3.5 weight percent, calculated as elemental sodium and based on the weight of the zeolite; at a temperature in the range of from about 120° C. to about 350° C. and at a pressure that is sufficiently high to maintain the feedstock substantially in the liquid phase, to thereby cyclize the first feedstock to form a liquid product comprising one or more dimethyltetralins, wherein water is at a concentration in the first feedstock of from zero up to less than about 0.5 weight percent, based on the weight of the feedstock, wherein (1) when the feedstock comprises 5-(o-toly)-pent-1- or -2-ene, at least 80 weight percent of the dimethyltetralin product formed is comprised of 1,5-, 1,6- 2,5- or 2,6-dimethyltetralin or a mixture thereof, (2) when the feedstock comprises 5-(m-toly)-pent-1- or -2-ene, at least 80 weight percent of the dimethyltetralin product formed is comprised of 1,5- 1,6- 1,7- 1,8-, 2,5-, 2,6-, 2,7- or 2,8- dimethyltetralin or a mixture thereof, (3) when the feedstock comprises 5-(p-tolyl)-pent-1- or -2-ene, at least 80 weight percent of the dimethyltetralin product formed is comprised of 1,7-, 1,8-, 2,7- or 2,8-dimethyltetralin or a mixture thereof, or (4) when the feedstock comprises 5-phenyl-hex-1- or -2-ene, at least 80 weight percent of the dimethyltetralin product formed is comprised of 1,3-, 1,4-, 2,3-, 5,7-, 5,8- or 6,7-dimethyltetralin or a mixture thereof;

(b) separating the resulting cyclization product mixture by distillation at reduced pressure into a lighter, lower boiling fraction that comprises the dimethyltetralin product and a heavier, higher boiling fraction boiling above the boiling point of the dimethyltetralin product, and withdrawing the resulting lighter fraction as distillation overhead; and (c) combining the resulting heavier fraction with a fresh supply of the tolyl-pentene(s) or phenyl-hexene(s) employed in step (a), cyclizing the resulting mixture under the cyclization conditions employed in step (a), and separating the resulting cyclization product mixture under the distillation conditions employed in step (b).

2. The method of claim 1 wherein in step (b), the heavier fraction boils above about 240° C. at 1 atmosphere.

3. The method of claim 1 wherein, when steps (a)-(c) are performed on a batch basis, from about 0.01 to about 2 parts by weight of the heavier fraction from step (b) are combined in step (c) per part by weight of fresh supply of tolyl-pentene(s) or phenyl-hexene(s).

4. The method of claim 3 wherein, from about 0.05 to about 0.35 parts by weight of the heavier fraction from step (b) are combined in step (c) per part by weight of the fresh supply of tolyl-pentene(s) or phenyl-hexene(s).

5. The method of claim 1 wherein, when steps (a)-(c) are performed continuously, from about 0.2 to about 20 parts by weight of the heavier fraction from step (b) are combined in step (c) per part by weight of the fresh supply of tolyl-pentene(s) or phenyl-hexene(s).

6. The method of claim 5, wherein from about 1 to about 5 parts by weight of the heavier fraction from step (b) are combined in step (c) per part by weight of the fresh supply of tolyl-pentene(s) or phenyl-hexene(s).

7. The method of claim 1 wherein, when steps (a)–(c) are performed on a batch basis, the sequence of steps (b) and (c) is repeated from one to about 100 times.

8. The method of claim 1 wherein, when steps (a)–(c) are performed continuously, a portion of the catalyst is periodically withdrawn and replaced with fresh catalyst.

9. The method of claim 1 wherein the following additional steps are performed:
 (d) cracking the resulting separated heavier fraction from step (c) in the presence of a solid cracking catalyst at a cracking temperature in the range of from about 120° C. to about 450° C., which temperature is at least 10° C. above the temperature employed for the cyclization of step (c) and at a pressure that is sufficiently high to maintain the heavier fraction being cracked substantially in the liquid phase; and
 (e) separating the resulting cracking product mixture by distillation at reduced pressure into a lighter, lower boiling fraction that comprises the dimethyltetralin product and a heavier, higher boiling fraction that boils above the boiling point of the dimethyltetralin product.

10. The method of claim 9 wherein the heavier fraction in step (e) boils above about 240° C. at one atmosphere.

11. The method of claim 9 wherein the cracking temperature in step (d) is in the range of from about 180° C. to about 330° C.

12. The method of claim 9 wherein the cracking temperature in step (d) is at least 30° C. above the cyclization temperature in step (c).

13. The method of claim 9 wherein the cracking catalyst comprises the catalyst employed for cyclization in steps (a) and (c).

14. The method of claim 9 wherein in step (e) the heavier fraction boils above about 240° C.

15. The method of claim 1 wherein said solid cyclization catalyst comprises an acidic, ultrastable Y-zeolite having a unit cell size in the range of about 24.2 to about 24.7 Angstroms, a silica-to-alumina bulk molar ratio in the range of about 4:1 to about 10:1, and a sodium content of about 0.05 to about 3.5 weight percent, calculated as elemental sodium.

16. The method of claim 1 wherein said solid cyclization catalyst comprises a relatively low acidity ultrastable Y-zeolite having a unit cell size of no more than about 24.3 Angstroms, a silica-to-alumina bulk molar ratio of at least about 12, and a sodium content of less than about 0.4 weight percent, based on the weight of the zeolite and calculated as elemental sodium.

* * * * *